United States Patent [19]
Pauli et al.

[11] Patent Number: 5,091,154
[45] Date of Patent: Feb. 25, 1992

[54] TEST CARRIER ANALYSIS SYSTEM

[75] Inventors: Manfred Pauli; Rudolf Schüssler, both of Mannheim, Fed. Rep. of Germany

[73] Assignee: Boehringer Mannheim GmbH, Mannheim, Fed. Rep. of Germany

[21] Appl. No.: 456,147

[22] Filed: Dec. 27, 1989

[30] Foreign Application Priority Data

Dec. 28, 1988 [DE] Fed. Rep. of Germany ....... 3844103

[51] Int. Cl.$^5$ ............................................. G01N 21/01
[52] U.S. Cl. ..................................... 422/63; 422/68.1;
422/82.05; 356/244
[58] Field of Search .................... 422/63, 68.1, 82.05; 356/244, 446, 416

[56] References Cited

U.S. PATENT DOCUMENTS

| | | | |
|---|---|---|---|
| 3,771,877 | 11/1973 | Rosencranz | 356/446 |
| 4,090,791 | 5/1978 | Siddigi et al. | 356/244 |
| 4,257,862 | 3/1981 | Schnipelsky et al. | 422/63 |
| 4,372,682 | 2/1983 | Nenninger et al. | 356/244 |
| 4,780,283 | 10/1988 | Meinecke et al. | 422/68 |
| 4,791,461 | 12/1988 | Kishimoto et al. | 356/446 |
| 4,927,603 | 5/1990 | Fischer et al. | 422/63 |
| 4,934,817 | 6/1990 | Gassenhuber | 356/446 |
| 4,985,205 | 1/1991 | Fritsche et al. | 422/68.1 |

FOREIGN PATENT DOCUMENTS

| | | |
|---|---|---|
| 0037484 | 10/1981 | European Pat. Off. . |
| 0129220 | 12/1984 | European Pat. Off. . |
| 0183524 | 6/1986 | European Pat. Off. . |
| 8716270 | 3/1988 | Fed. Rep. of Germany . |

Primary Examiner—Robert J. Warden
Assistant Examiner—Laura E. Collins
Attorney, Agent, or Firm—Armstrong, Nikaido, Marmelstein, Kubovcik & Murray

[57] ABSTRACT

Test carrier analysis system consisting of test carriers and an associated evaluation apparatus.

The evaluation apparatus has a positioning device (5) for the exact positioning of a test carrier (1). A fixing element engaging with a recess (8) of the test carrier (1) is used for this purpose.

Improved handling properties with lowest possible design outlay and good positional accuracy are achieved by the fact that the positioning device (5) comprises a stop (17) for the introduction end (1a) of the test carrier (1), the test carrier rest (6) supports the test carrier (1) at least in the vicinity of the recess (8) in a level plane, the fixing element (9) comprises a bit stop (9b) limiting its depth of penetration into the recess (8) and the actuating organ (10) of the fixing element (9) is so designed and disposed that in the measurement position a force is exerted on the test carrier (1) which has both a component parallel to the surface of the latter in direction onto the stop (17) and a component normal to its surface in direction onto the test carrier rest (6).

14 Claims, 2 Drawing Sheets

TEST CARRIER ANALYSIS SYSTEM

The invention relates to a test carrier analysis system, consisting of test carriers and an associated evaluation apparatus, where the test carriers have at least one recess and the evaluation apparatus comprises a positioning device for positioning a test carrier in the measurement position and where the positioning device comprises a rest for the test carrier and a fixing element which in the measurement position engages positively with the recess of the test carrier and is combined with an actuating organ.

Test carrier analysis systems are increasingly used for the analysis of fluids, in particular body fluids such as blood or urine. The test carriers have test layers containing one or more reagents. If the latter are brought into contact with the sample, a reaction takes place which finally leads to a detectable signal, in particular to a colour change in a test layer.

The evaluation apparatuses are designed for the test carriers, with which they form a system. A distinction is drawn between single-parameter systems, with which only one specific analysis (for example, glucose in the blood), can be carried out and multi-parameter systems which operate with several different types of test carrier designed for one particular analysis, which are all evaluated with the same apparatus.

There are various forms of test carriers. Essentially square platelets, also known as slides, are known in particular, in the centre of which a multi-layered layer composite is situated. Other test carriers are designed as elongated test strips, on the base, plastics layer of which the test layers are arranged. The invention relates in particular to test carriers of the last-named kind.

The positioning of the test carriers in the evaluation apparatus is a factor which should not be underestimated, both as regards the accuracy of the analysis and the simplicity of the handling. With the usual reflection-photometric measurements it is immediately obvious that the main consideration is the distance of the test layer from the measurement optics. But very strict tolerances also have to be observed in the longitudinal and transverse direction of the test carrier, particularly as the test layer areas are being increasingly reduced in order to economize on reagents, while on the other hand considerations of measurement accuracy require that the evaluation be based on the largest possible part of the test layer as a measurement area.

A test carrier analysis system of the kind described at the outset is known from EP-A 129 220 (and U.S. Pat. No. 4,780,283. The strip-shaped test carriers used there have a hole both at the end with which they are introduced into the apparatus (introduction end) and at the other end (handling end). Two pinshaped fixing elements are accordingly provided on the apparatus, which engage positively with the corresponding hole of the test carrier. Very high accuracy of the positioning is achieved with the known device by the test carrier being under tension in the longitudinal position. For this purpose the fixing element assigned to the handling end of the test carrier is provided with a spring.

Although the known device permits accurate positioning, the handling is comparatively cumbersome, because the test carrier has to be fixed at both ends in turn. Also the construction is relatively complicated.

In order to provide a test carrier analysis system of the kind described at the outset with improved handling properties with lowest possible design outlay and with very good positional accuracy, it is proposed according to the invention that the positioning device comprise a stop against which the test carrier comes to rest with its front end in the introduction direction, the test carrier rest is so designed that it supports the test carrier in the measurement position at least in the region of the recess in a level plane, the fixing element comprises a bit stop limiting the depth of penetration into the recess and the actuating organ is so arranged and designed that the test carrier is in the measurement position force-loaded both parallel to its surface in direction onto the stop and normal (vertically) thereto in direction onto the test carrier rest.

Reliable and accurate positioning of the test carrier can therefore be achieved in all three spatial directions with only one moving part. Only one recess in the vicinity of the introduction end of the test carrier is required. The introduction is simplified and the handling end of the test carrier remains unobstructed. Surprisingly, adequate flatness is nevertheless obtained to permit thermostatting of the measurement area by means of a hot-plate situated in the test carrier rest.

Particular preference is given to an embodiment of the invention in which a swivellable lever arrangement is used as actuating organ. Although the actuation of the fixing element via a lever arrangement is known from the above-cited EP-A 129220, the design and arrangement of the latter shows major differences in the present invention, as will be explained in greater detail below. A positioning of the test carrier which is particularly simple in design and nevertheless particularly easy to operate is thereby made possible.

BRIEF DESCRIPTION OF THE DRAWINGS

The invention will be described in greater detail below by means of an exemplifying embodiment shown diagramatically in the figures, where

FIGS. 1 and 2 serve to explain the inventive principle by means of an initial embodiment. The test carrier 1 is situated in the measurement position, i.e. its detection layer 2 with the measurement surface 2a is located exactly below the measurement opening 3, shown only as an indication by dashed lines, of an optical unit 4. The test carrier 1 lies with its bottom side on a test carrier rest 6, which is fixed to a frame part 7 of the apparatus.

Figure 1:
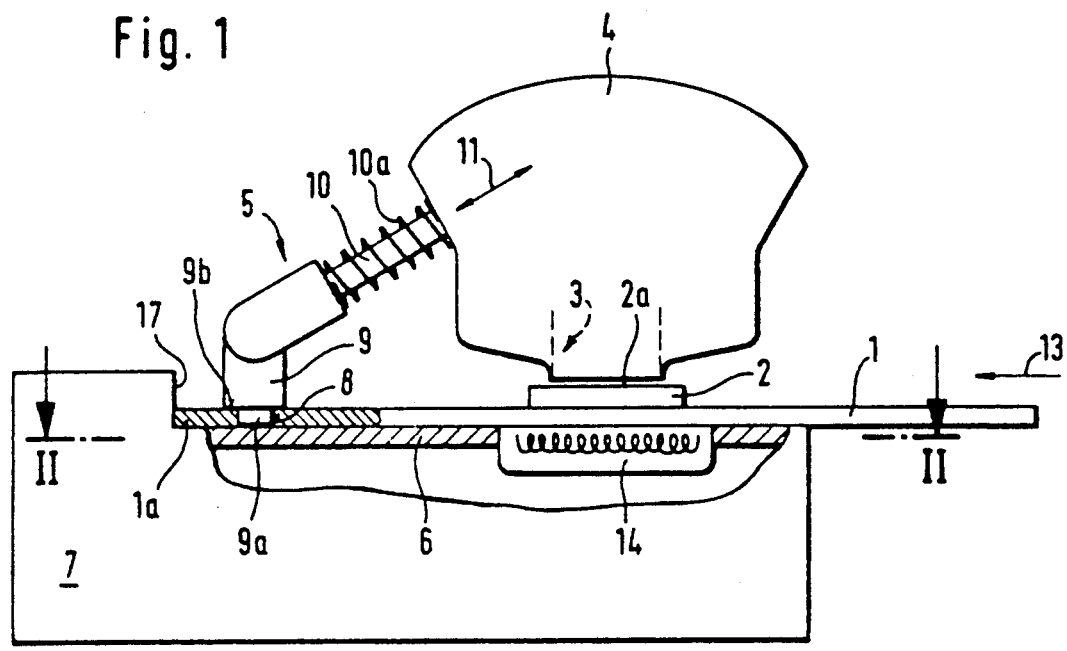
FIG. 1 is a side-view onto the evaluation part of a test carrier analysis system according to the invention in the measurement position.

The test carrier 1 is introduced in the figure from right to left into the positioning device designated overall as 5. In the vicinity of its front end, which is also designated as introduction end Ia, is located a recess 8 which is suitably designed as a circular hole, but can also have another shape.

In the recess 8 there engages as fixing element a pin 9 which is fastened to an actuating rod 10 which in its turn is movable axially in the direction of the arrow 11. For this purpose there can be provided—as represented—a pressure spring 10a surrounding the actuating rod 10 and an electro-magnet accomodated in the present case in the housing of the optical unit and not represented in the figure. Details of the concrete realization of the actuating organ for the fixing element 9 are of no concern here. The expert is well acquainted with alternatives, for example a spindle drive consisting of an electric motor. Essential for the invention, however, is the fact that the fixing pin 9 is acted on by a force which has a component parallel to the test carrier surface in the introduction direction designated by the arrow 13 and a normal component acting from above onto the test carrier surface.

In order to transfer this force onto the test carrier 1, the fixing element 9 is of smaller cross-section at its front end 9a penetrating into the recess 8 than further behind. At the transition point a bit stop is produced in the form of a circular supporting surface 9b which butts against the edge of the recess 8. It is also important that the test carrier rest 6 supports the test carrier located in the measuring position at least in the vicinity of the recess and below the measurement surface in a level plane. In the case represented the test carrier rest 6 is designed as a continuous rest surface with a flush-recessed hot-plate 14 for the tempering of the detection layer 2. It would be sufficient, however, if the regions 15 and 16 represented by dashes in FIG. 2 formed a level rest. This could be appropriate, for example, if other components of the apparatus (for example, a reading head for recognizing a code applied to the test carrier) were to be installed between these regions.

Finally, the stop 17 represents an important element of the invention. It limits movement of the test carrier in the introduction direction 13. The stop 17 is located substantially at right angles to the plane of the test carrier rest 6 and is suitably designed as a level rest surface, as shown, against which the front edge of the test carrier (shown in dashes in FIG. 2) butts over its entire length. This produces an alignment of the test carrier longitudinal axis. Alternatively, however, a more or less dot-shaped stop can also be provided, in which case the alignment of the test carrier is ensured by lateral guidance of its longitudinal edges (1b, 1c in FIG. 2).

Figure 2:
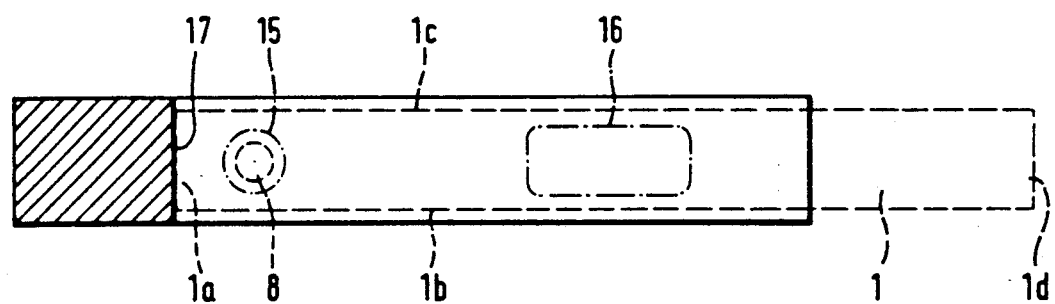
FIG. 2 is a section along the line II—II of FIG. 1.

It is advantageous, as shown in FIGS. 1 and 2, for the test carrier rest 6 to be shorter than the length of the test carrier 1. The handling end 1d of the latter thereby projects beyond the test carrier rest 6, which facilitates the introduction and removal.

In order to introduce the test carrier, the positioning device is brought into an introduction position not represented in FIGS. 1 and 2 in which the optical unit 4 is raised vertically upwards and the actuating rod 10 drawn into the housing of the optical unit 4. In this position the test carrier 1 is introduced in the direction of the arrow 13 up to the stop 17. The optical unit 4 is then lowered until its measurement opening 3 is just above the measurement surface 2. In this position the retaining rod 10 is moved downwards to the left out of the optical unit 4 in the figure, the fixing rod 9 then engaging with the recess 8 and pressing the test carrier in the mentioned direction to the left against the stop 17 and downwards against the test carrier rest 6. The test carrier 1 is thereby fixed exactly. The optical unit 4 is lowered into the final measurement position.

Figure 3:
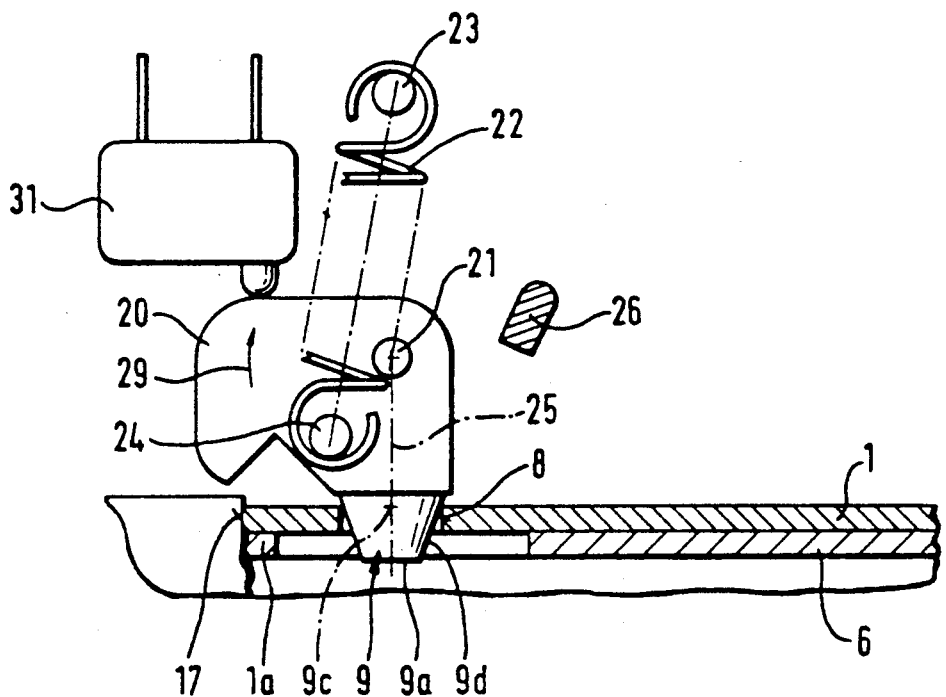
FIG. 3 is a side-view of the main functional elements of a preferred embodiment in the measurement position.
Figure 4:
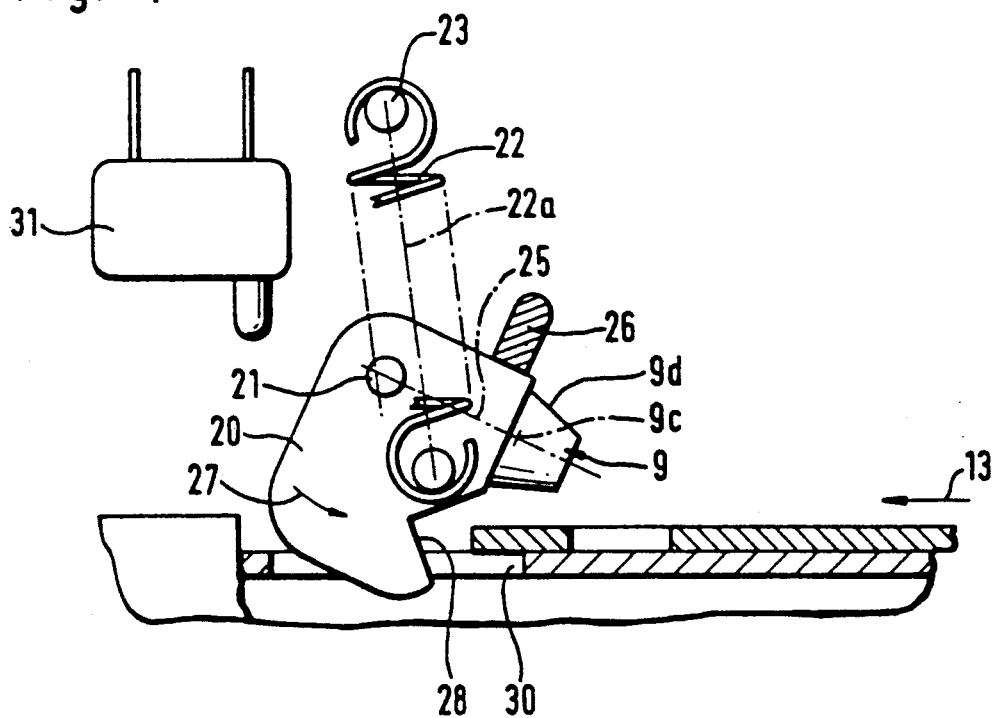
FIG. 4 is a view according to FIG. 3 in the introduction position.

FIGS. 3 and 4 show by way of example an embodiment of the invention in which a swivellable lever arrangement is used as actuating organ for the fixing element.

The lever arrangement is suitably, as shown, designed as an actuating disc 20 which is swivellable about a swivelling axis 21 running parallel with the test carrier surface 6 and perpendicular to the introduction direction 13. The fixing element 9 is connected firmly to the actuating disc 20 and preferably made of one piece with the latter. In order to facilitate the penetration into the recess 8 of the test carrier 1, the fixing element tapers conically towards the front end 9a. The diameter of the cone is greater at its thickest point than the diameter of the recess 8, so that the expanding outer surface 9d of the cone acts as a bit stop which limits the depth of penetration (FIG. 3).

The actuating disc 20 is subject to the force exerted by a tension spring 22 which is fastened on the one hand firmly to the apparatus by an upper articulation point 23 and on the other to the actuating disc 20 by a lower articulation point 24. The spring 22 is so articulated on the actuating disc, aligned and dimensioned as to its resilience that adequate force-loading in the above-mentioned direction, i.e. in the introduction direction 13 and normal thereto in direction onto the test carrier rest 6, is achieved.

The connecting line 24 between the swivelling axis (21) of the lever arrangement (20) and the center (9c) of the bit stop (9d) of the fixing element (9) is approximately vertical in the measurement position. The above identified force-loading of the test carrier (1) is in the preferred embodiment represented in FIG. 3 achieved by the spring (22) engaging substantially vertically from the test carrier rest upwards with an articulation point 24 which is displaced from the connecting line 25 towards stop 17.

In principle the mentioned spring effect can however also be achieved, in another manner, for example by means of a down-ward-acting tension spring which engages with an articulation point which is displaced opposite the connecting line 25 away from the stop 17 (i.e. to the right in FIG. 3).

The actuating disc 20 can be moved for example by an electric motor. Particularly preferable however, because of its simplicity, is actuation by the test strip itself, as represented in FIGS. 3 and 4.

In this case the swivelling point 24 of the spring 22 is so disposed on the actuating disc 20 that the spring passes during the swivelling of the actuating disc 20 trough a state of maximum spring tension which corresponds to an apex of the force driving the swivelling movement, so that the spring force acts on both sides of the apex away from the latter.

FIG. 4 shows the introduction position of the positioning device, the actuating disc 20 resting against a swivel stop 26 which limits the swivel path in the introduction position. The axis 22a of the spring 22 crosses the above-defined connecting line 25, so that a force is exerted in the direction of the arrow 27.

The actuating disc 20 has a contact surface 28 which is so disposed that a test carrier 1 introduced in the direction of the arrow 13 butts against it and exerts a corresponding torque in the direction of the arrow 29. The actuating disc is thereby swivelled into the measurement position (FIG. 3). The test carrier rest 6 suitably comprises a recess 30 (here in the form of a longitudinal slot) with which the actuating disc engages.

The distance between the contact surface 28 and the fixing pin 9 is adapted to the distance between the introduction end 1a and the recess 8 of the test carrier 1. The fixing pin 9 thereby engages with the recess during the swivelling process. At approximately the same time the apex (point of maxiumum extension of the spring 22) is exceeded. The spring force then acts in the direction of the arrow 29 until the introduction end 1a of the test carrier 1 butts against the stop 17. It is preferable for the upper swivelling point 23 of the spring 22 to be disposed roughly in the prolongation of the connecting line 25, while the lower swivelling point is displaced relative to this connecting line in direction onto the stop 17. A comparatively powerful spring will be used, which is pre-loaded in the fitted position, i.e. is tensioned also in the positions of minimum spring tension at both ends of the swivel path. A relatively short powerful spring with a spring coefficient (C value) of at least about 0.2 N/mm is preferred, which is preloaded in such a way that the resulting spring force is at least about 1 N. In order to produce ease of actuation, the contact surface 28 is situated farther from the swivel axis 21 than the articulation point 24 of the spring 21.

When the measurement position is reached, a microswitch 31 is actuated by the actuating disc 20 in order to signal to the evaluation circuit of the apparatus the reaching of the measurement position. The microswitch 31 does not however limit the swivel path of the actuating disc 20 in the measurement position.

The latter is limited instead only by the butting of the introduction end 1a against the stop 17.

The expert will be acquainted with numerous variations of the design elements represented here. Thus it is possible to use as a lever arrangement, instead of the represented actuating disc, any other lever design which results overall in a corresponding swivelling movement of the described articulation or stop points and the fixing element about a swivelling axis. The fixing element does not have to be permanently connected rigidly to the lever arrangement. It is sufficient if a firm connection is made in the measurement position such that the force transmission according to the invention is achieved. Finally, another known spring element, for example on a pneumatic basis, can be used instead of the represented spring.

The measurement of the detectable change of the test carrier is preferably by an optical unit, as described above, but it will be clear from those in the art that other types of determination of detectable changes can be utilized. Suitable circuitry and apparatus for such an optical unit determination is described in U.S. Pat. Nos. 4,553,848 and 4,523,853, the disclosure of which is hereby incorporated by reference.

We claim:

1. Evaluation apparatus for detecting a detectable change of a test carrier caused by contacting the test carrier with a fluid sample
said apparatus comprising: detecting means for detecting a detectable change,
and positioning means for accurately positioning a test layer of a test carrier having a front end, a rear end and at least one recess located intermediate the front end and the rear end in a relationship to the detecting means in a measurement position,
said positioning means including rest means for supporting the test carrier in the measurement position at least in the vicinity of a recess in a level plane, stop means for positioning the front end of the test carrier when the front end is inserted into the apparatus to abut against the stop means, and fixing means connected to an actuating element for positive penetrating engagement with the test carrier recess when the test carrier is in the measurement position, said fixing means including a bit stop which limits the depth of penetration of the fixing means into the recess, said fixing means also including means for simultaneously transmitting force from the actuating element to the test carrier to force-load the test carrier both parallel to the surface thereof in the direction toward said stop means and normal to the surface thereof in a direction toward said rest means.

2. Apparatus of claim 1, wherein the test carrier is elongated, and the rest means is shorter than the test carrier in the elongated direction so that the rear end of the test carrier projects beyond the rest means when the test carrier is in the measurement position.

3. Apparatus of claim 1, wherein a portion of the fixing means penetrates the test carrier recess, and said portion is conical in shape.

4. Apparatus of claim wherein the actuating element includes a spring, a lever disposed above the test carrier and swivellable about a swiveling axis under the force exerted by the spring, the fixing means at least when in the measurement position being positionally stable with respect to the lever, said spring being articulated to the lever and aligned and dimensioned as to the spring force to produce the desired loading of the test carrier in the measurement position.

5. Apparatus of claim 4, wherein the bit stop has a center which with the swiveling axis defines a connecting line in the measurement position of the apparatus which is approximately vertical.

6. Apparatus of claim 4, wherein the spring is articulated to the lever at an articulation point which is disposed in relation to the swiveling axis to cause the spring during swiveling of the lever to pass through a state of maximum spring tension which corresponds to an apex of the swiveling movement, with the spring force being exerted away from the apex on both sides thereof.

7. Apparatus of claim 6, wherein the apparatus includes swivel stop means for limiting the travel of the lever when the lever is moved out of the measurement position.

8. Apparatus of claim 7, wherein the lever includes contact surface means for the test carrier to abut against to move the lever when the test carrier is introduced into the apparatus.

9. Apparatus of claim 4, wherein the rest means includes a surface, and recess means in the surface for receiving a portion of the lever.

10. Apparatus of claim 8, wherein the contact surface means is located further from the swiveling axis than the spring articulation point.

11. Apparatus of claim 4, further including a microswitch positioned to be actuated by the lever when the lever is in the measurement position.

12. Apparatus of claim 4, wherein the articulation point of the spring to the lever is displaced in relation to the swivelling axis to produce an over-center relationship therebetween, with the swivelling axis being disposed on one side of the axis of the spring in the measurement position, and on the opposite side of the axis of the spring when no test carrier is in the apparatus.

13. Test carrier analysis system comprising at least one test carrier and an associated evaluation apparatus, said test carrier having a front end, a rear end, and at least one recess located intermediate the front end and the rear end, and including at least one test layer which when brought into contact with a fluid having a component to be determined will undergo a reaction to produce a detectable signal, said apparatus including detecting means for detecting at least one signal from a fluid sample, and
positioning means for accurately positioning the test carrier in relationship to the detecting means in a measurement position, said positioning means including rest means for supporting the test carrier in the measurement position at least in the vicinity of the test carrier recess in a level plane, stop means for positioning the front end of the test carrier in a predetermined position when the front end of the test carrier is inserted into the apparatus to abut against the stop means, and fixing means connected to an actuating element for penetrating engagement with the test carrier recess when the test carrier is in the measurement position, said fixing means including a bit stop which limits the depth of penetration of the fixing means into the recess, said fixing means also including means for simultaneously transmitting force from the actuating element to the test carrier to force-load the test carrier both parallel to the surface of the test carrier in the direction toward the stop means, and perpendicular to the surface thereof in a direction toward the rest means.

14. Test carrier analysis system of claim 13, in which said recess is located close to said front end.

* * * * *